United States Patent [19]
Harrawood et al.

[11] Patent Number: 5,230,112
[45] Date of Patent: Jul. 27, 1993

[54] PATIENT SUPPORT TABLE

[75] Inventors: Larry E. Harrawood, Sandy; James R. Harvey, Salt Lake City; Blain Erikson, Summit Park, all of Utah

[73] Assignee: Diasonics, Inc., Milpitas, Calif.

[21] Appl. No.: 916,509

[22] Filed: Jul. 20, 1992

Related U.S. Application Data

[63] Continuation of Ser. No. 616,677, Nov. 21, 1990, Pat. No. 5,131,105.

[51] Int. Cl.$^5$ .............................................. A61G 13/00
[52] U.S. Cl. .......................................... 5/607; 5/608; 5/610; 5/611
[58] Field of Search ..................... 5/607, 608, 610, 611

[56] References Cited

U.S. PATENT DOCUMENTS

| | | | |
|---|---|---|---|
| 2,172,941 | 9/1939 | Manning et al. | 311/7 |
| 3,281,598 | 10/1966 | Hollstein | 250/57 |
| 3,778,049 | 12/1973 | Viamonte, Jr. | 269/323 |
| 3,814,414 | 6/1974 | Chapa | 269/323 |
| 3,843,112 | 10/1974 | McDonald | 269/322 |
| 3,927,326 | 12/1975 | Kunne et al. | 250/447 |

(List continued on next page.)

FOREIGN PATENT DOCUMENTS 2126312 12/1972 Fed. Rep. of Germany .

OTHER PUBLICATIONS

Document entitled "Penta-Max I Special Procedures Table System," Spectrum X-Ray Corporation, Westville, N.J. (undated, but believed to be published around Jun. 1988).
Publication entitled "Bedalix Digital Table," Tecnomed USA, Bayshore, N.Y. (undated, but believed to be published around Oct. 1984).
Advertisement for PTCA/OR Table, Siemens Medical Systems (undated).
Advertisement for an x-ray system for whole body examination in angiography and interventional procedures, Siemens AG, Germany (undated).
Advertisement for an angiography whole body system, Shimadzu Europa GmbH, Germany (undated).
Marketing brochure entitled "Intraoperative Angiographic/Surgical Table, Model 206", Angiographic Devices Corp., Littleton, Mass. (undated but published in 1987).

*Primary Examiner*—Bruce M. Kisliuk
*Assistant Examiner*—Eileen Morgan
*Attorney, Agent, or Firm*—Blakely, Sokoloff, Taylor & Zafman

[57] ABSTRACT

A patient support table comprising a first patient support surface. The first patient support surface, in a preferred embodiment, is comprised of an x-ray translucent material such as carbon fiber. In a preferred embodiment, the top of the first patient support surface is for supporting a patient and is slightly concave. The patient support table also comprises a support, with the support being affixed to the first end of the first patient support surface at a first end of the support and extends beyond the third end of the first patient support surface. The support is affixed in such a manner that the first patient support surface may be interchanged with a second patient support surface, wherein the second patient support surface has all of the properties of the first patient support surface. The patient support table also comprises a base. The base is affixed to a second end of the support. The base allows positive and negative longitudinal tilt (Trendelenberg and reverse Trendelenberg), positive and negative lateral tilt, and height movement of the first patient support surface. The base provides a means for rigidly supporting the first patient support surface at a predetermined attitude and position.

64 Claims, 11 Drawing Sheets

U.S. PATENT DOCUMENTS

| | | | |
|---|---|---|---|
| 4,103,170 | 7/1978 | Spradlin | 250/451 |
| 4,146,793 | 3/1979 | Bergstrom et al. | 250/444 |
| 4,148,472 | 4/1979 | Rais et al. | 269/325 |
| 4,223,862 | 9/1980 | Doughty | 248/222.3 |
| 4,312,912 | 1/1982 | Tamura | 428/244 |
| 4,387,888 | 6/1983 | Marinakis | 269/324 |
| 4,426,715 | 1/1984 | Baer et al. | 378/4 |
| 4,426,725 | 1/1984 | Grady | 378/196 |
| 4,484,343 | 11/1984 | Cesar | 378/196 |
| 4,503,552 | 3/1985 | Miyahara et al. | 378/196 |
| 4,527,787 | 7/1985 | Collis, Jr. | 269/322 |
| 4,540,165 | 9/1985 | Green et al. | 269/325 |
| 4,541,108 | 9/1985 | Grady et al. | 378/196 |
| 4,545,571 | 10/1985 | Chambron | 269/322 |
| 4,550,421 | 10/1985 | Louiday | 378/196 |
| 4,576,368 | 3/1986 | Ogawa et al. | 269/322 |
| 4,602,378 | 7/1986 | Kelman et al. | 378/26 |
| 4,613,121 | 9/1986 | Hahn | 269/322 |
| 4,615,042 | 9/1986 | Schmedemann | 378/209 |
| 4,715,057 | 12/1987 | Hahn et al. | 378/197 |
| 4,715,591 | 12/1987 | Dragmen, Sr. | 269/322 |
| 4,718,077 | 1/1988 | Moore et al. | 378/209 |
| 4,727,564 | 2/1988 | Mekker et al. | 378/197 |
| 4,854,016 | 8/1989 | Rice | 24/495 |
| 4,860,394 | 8/1989 | Benessis et al. | 5/62 |
| 4,866,751 | 9/1989 | Louiday | 378/196 |
| 4,912,754 | 3/1990 | Van Steenburg | 378/209 |
| 5,048,071 | 9/1991 | Van Steenburg | 378/209 |

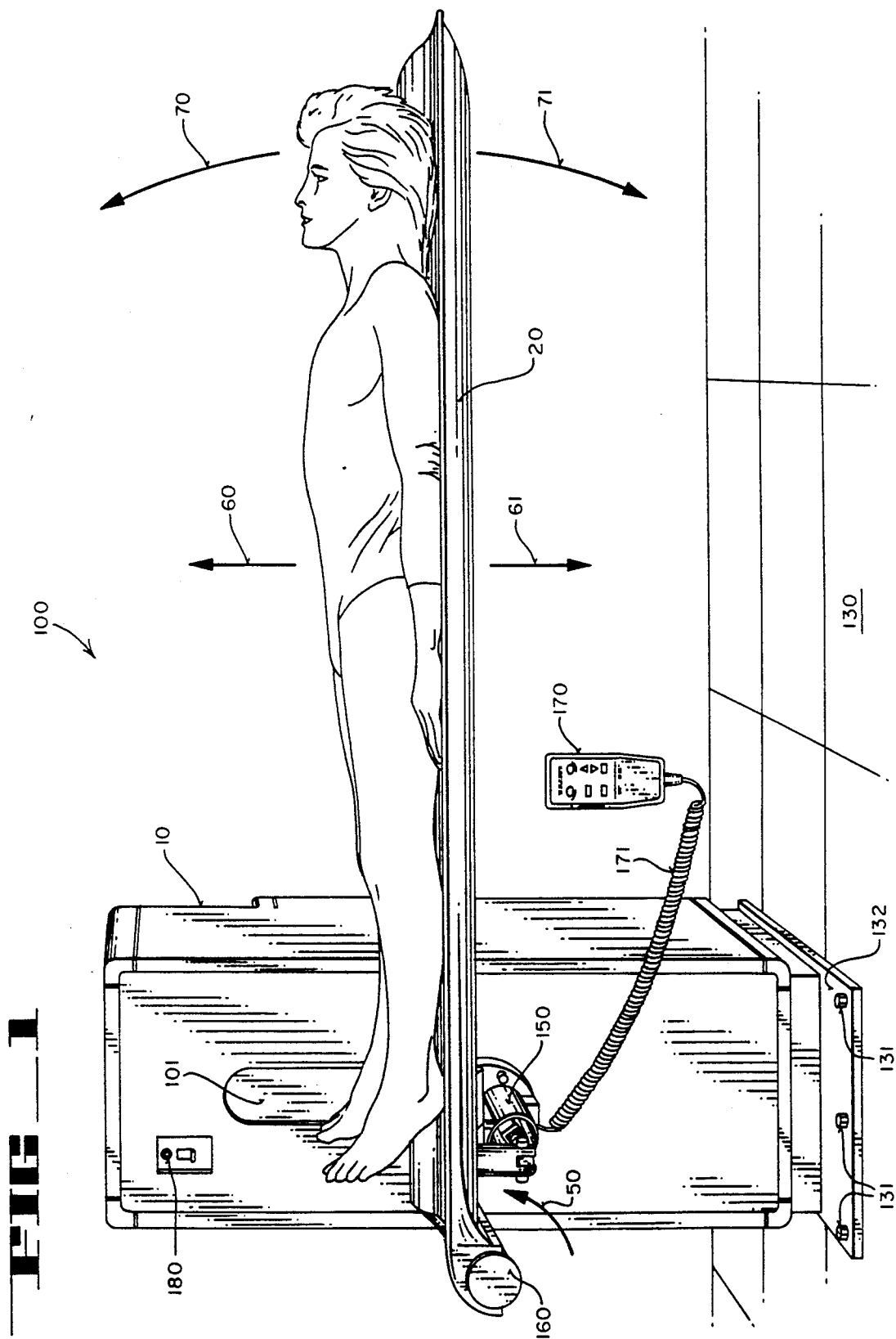

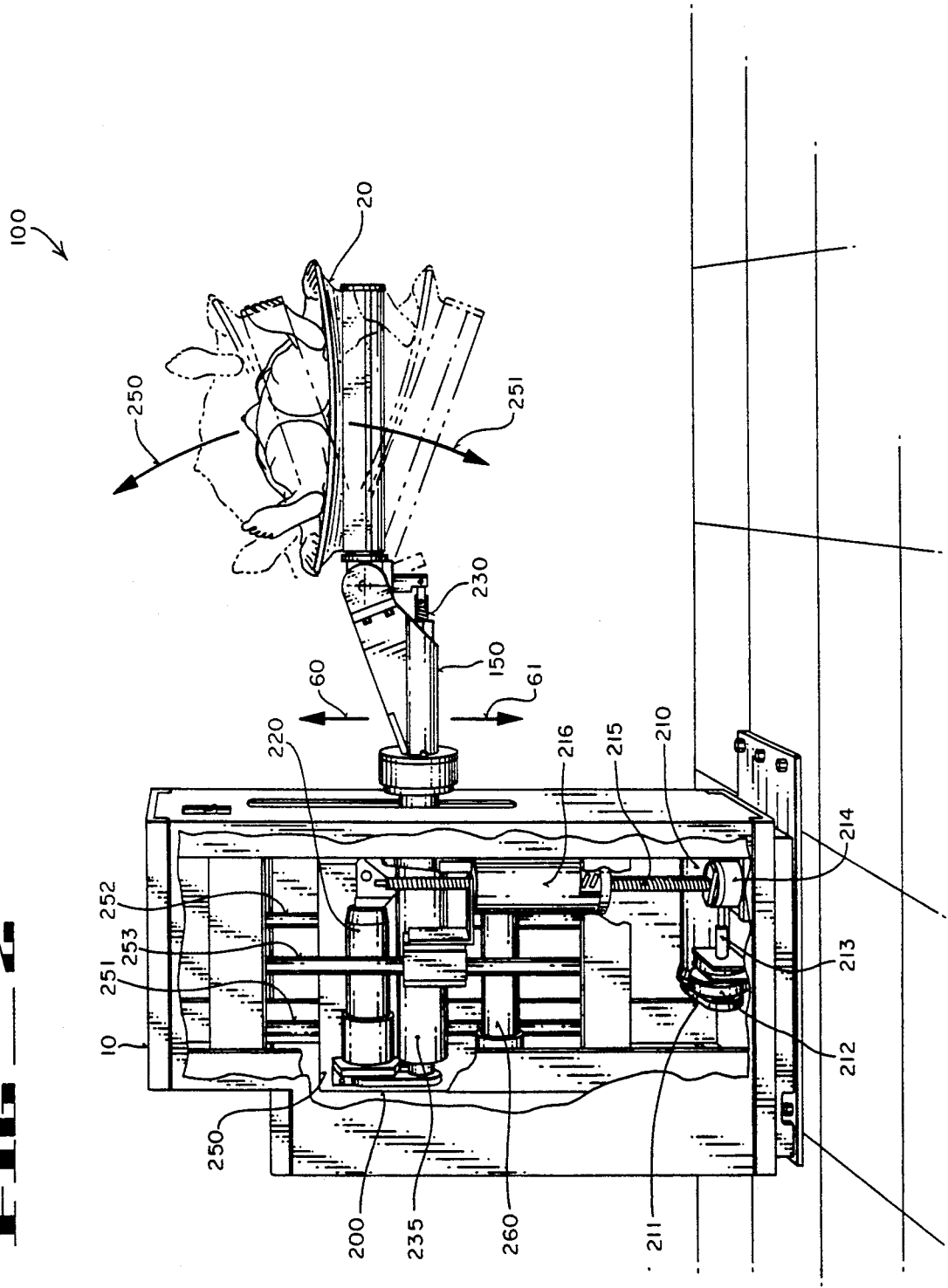
FIG_2

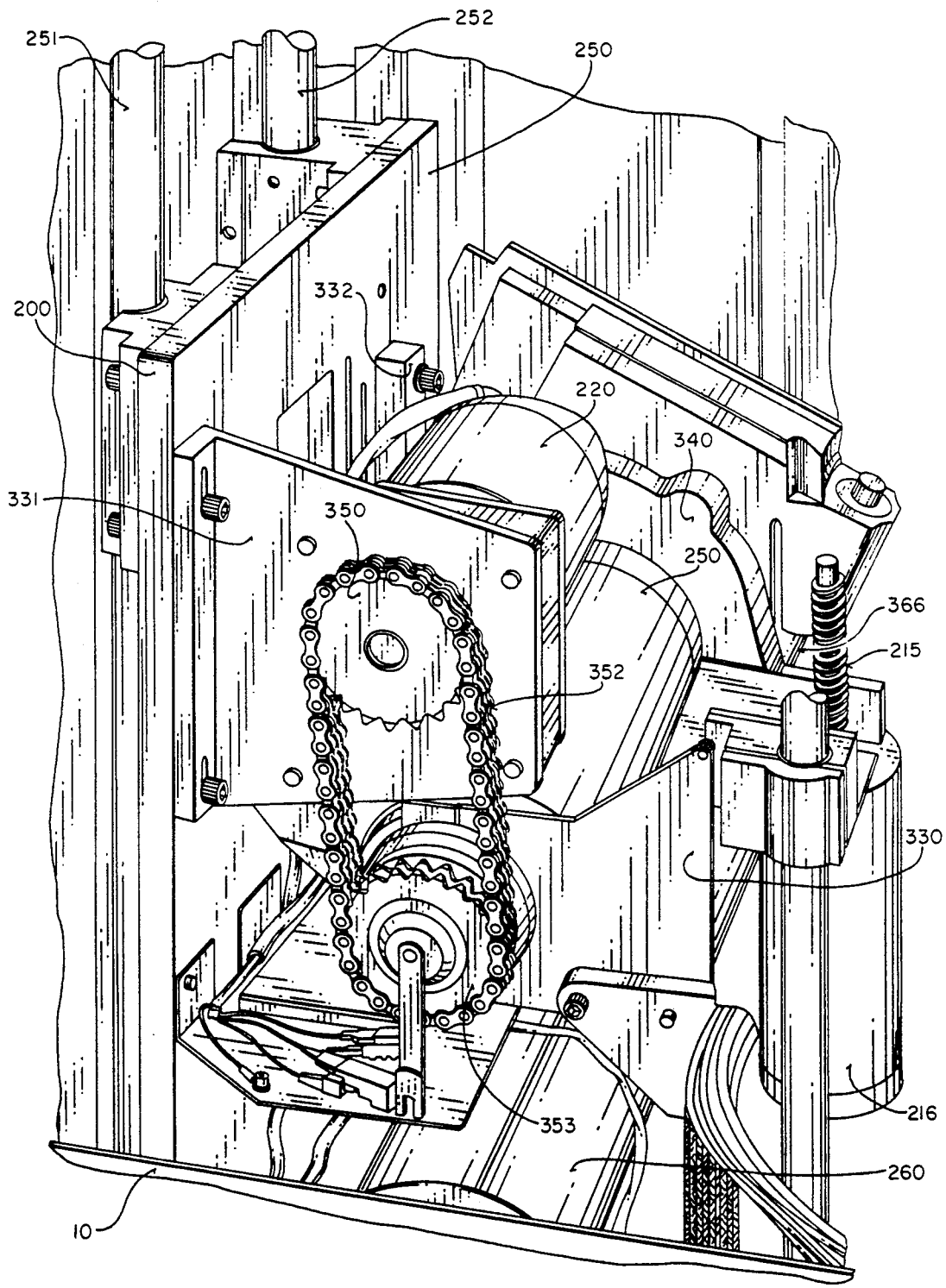

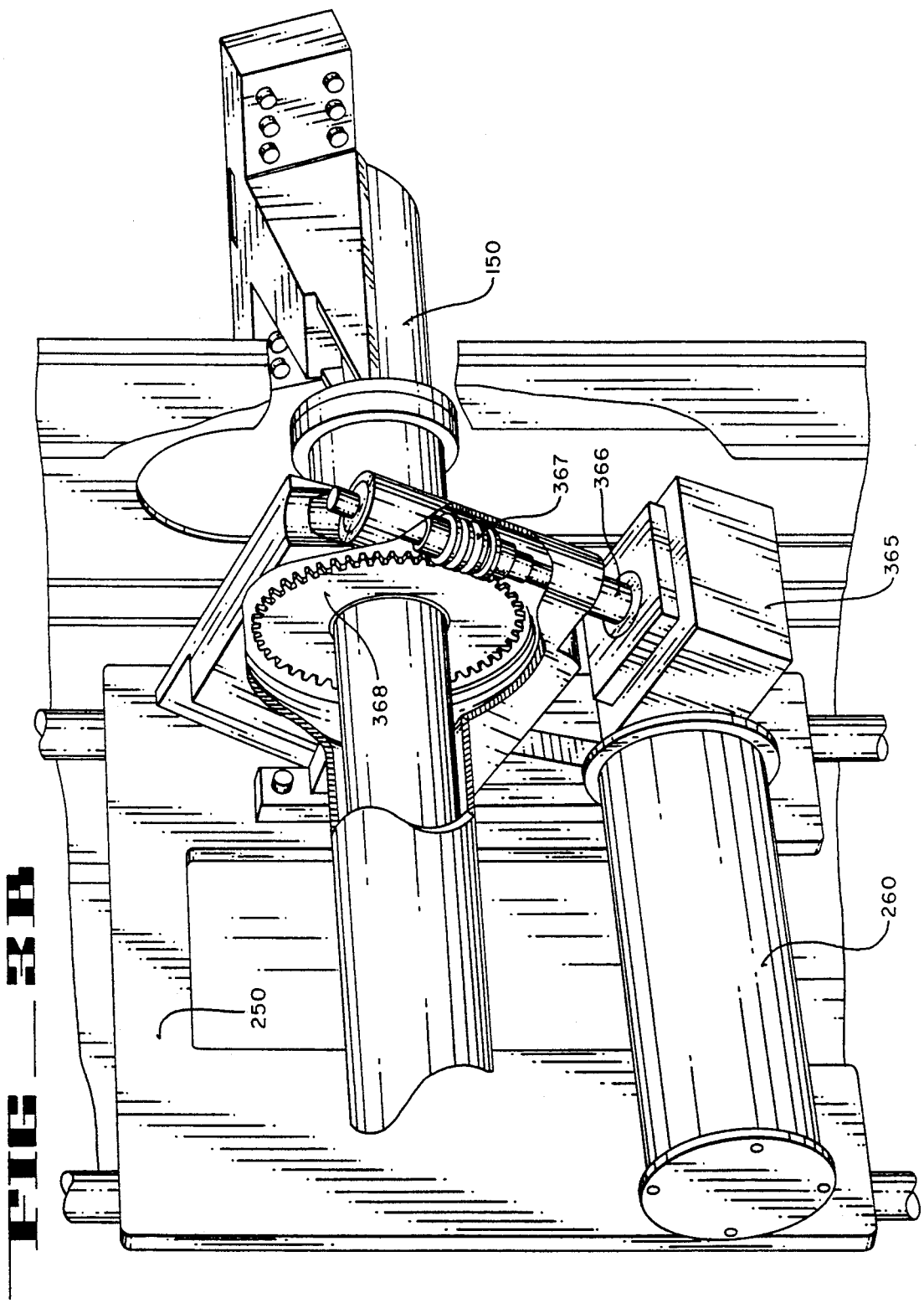

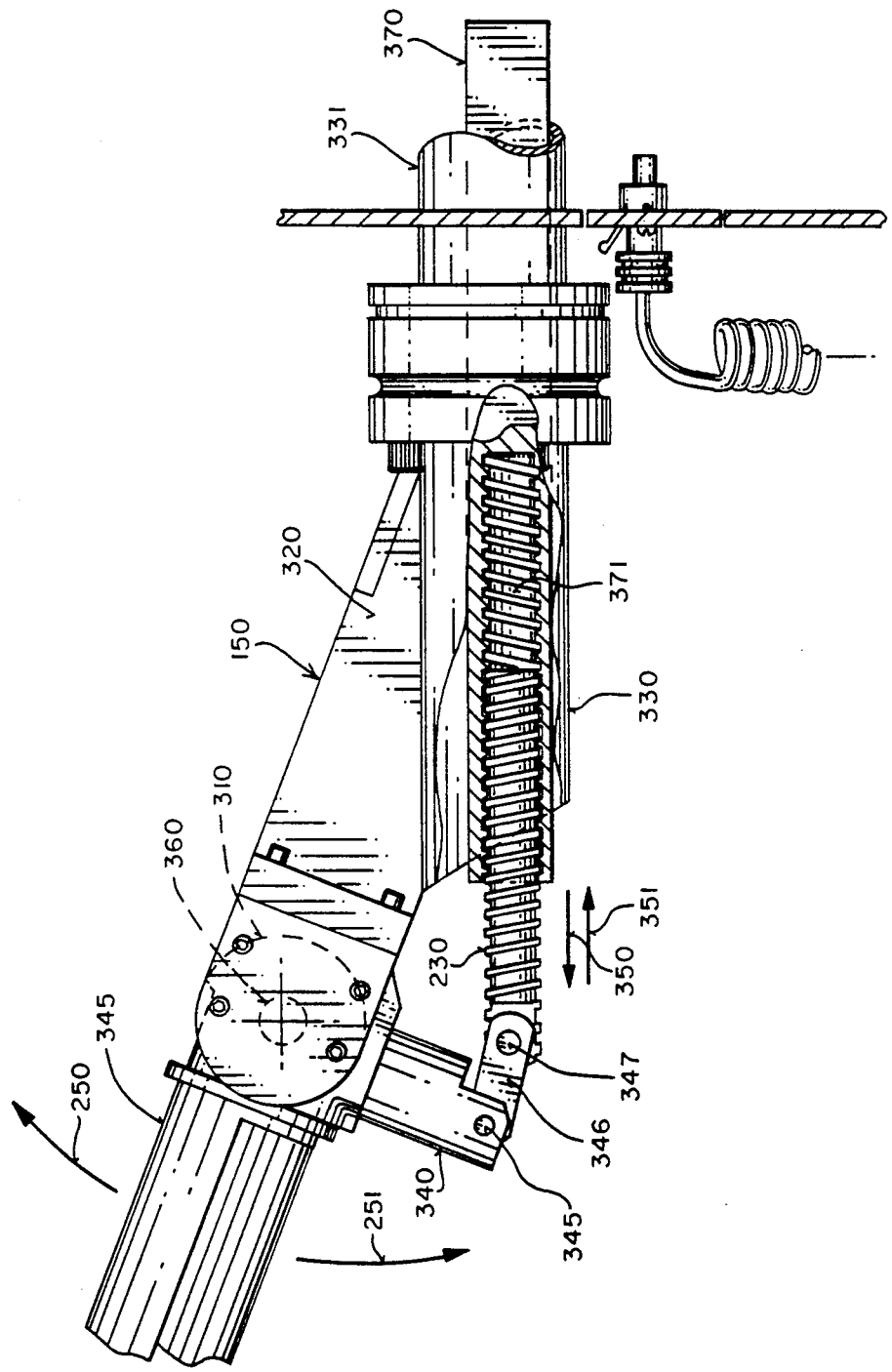

FIG_4
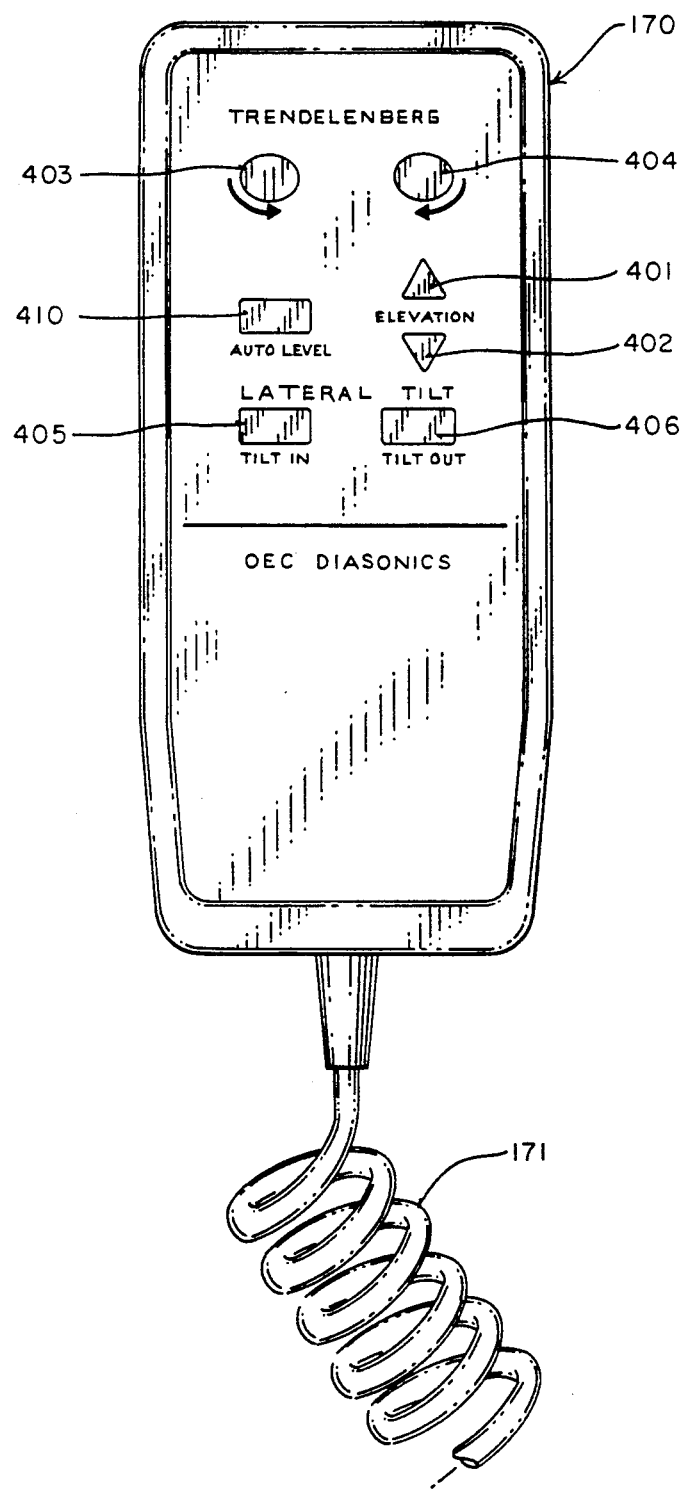

FIG_5A
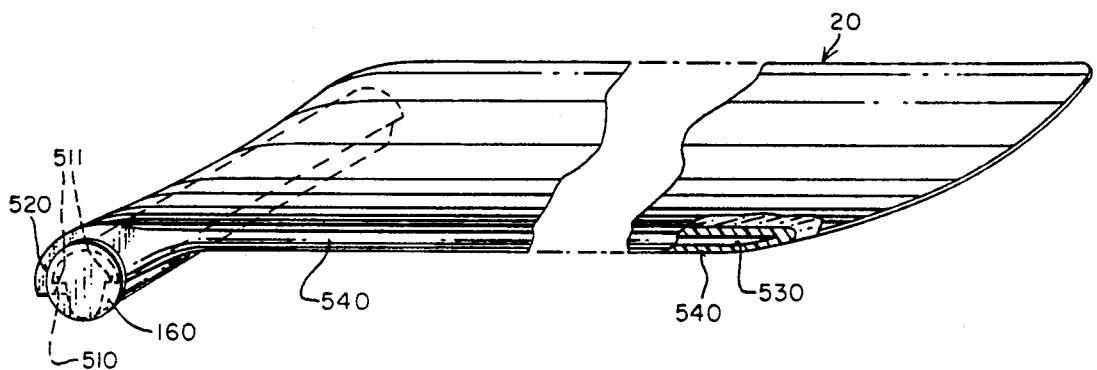
FIG_5B
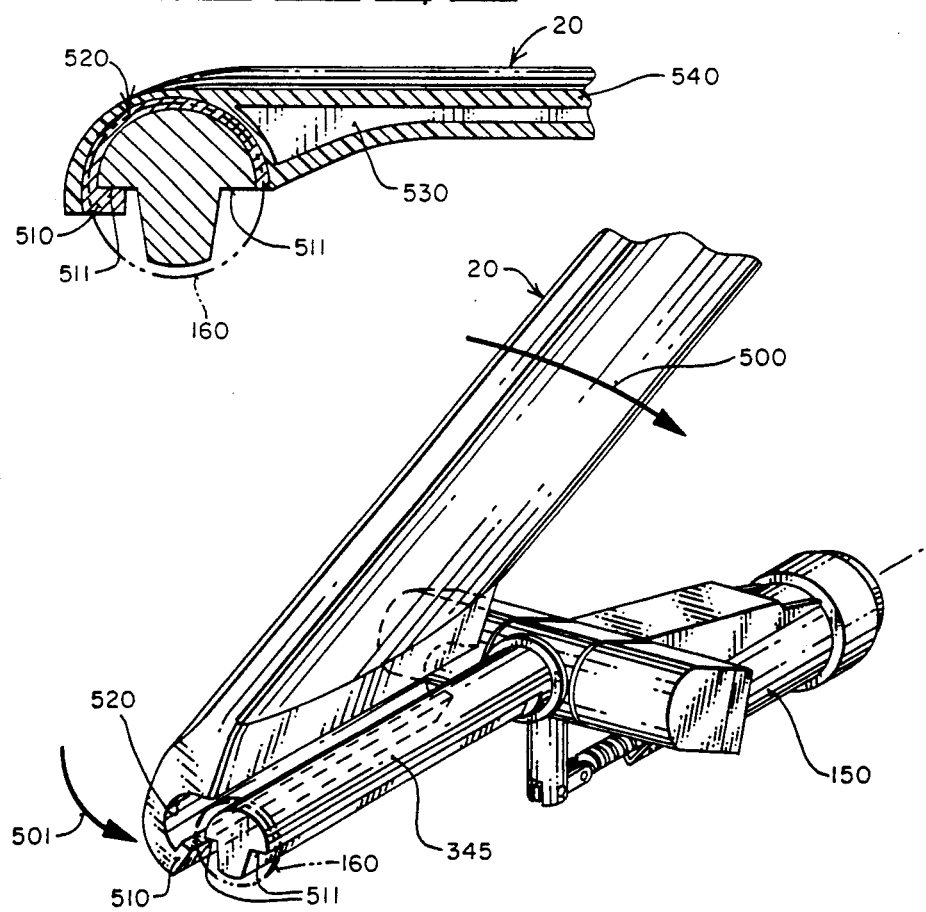
FIG_5C

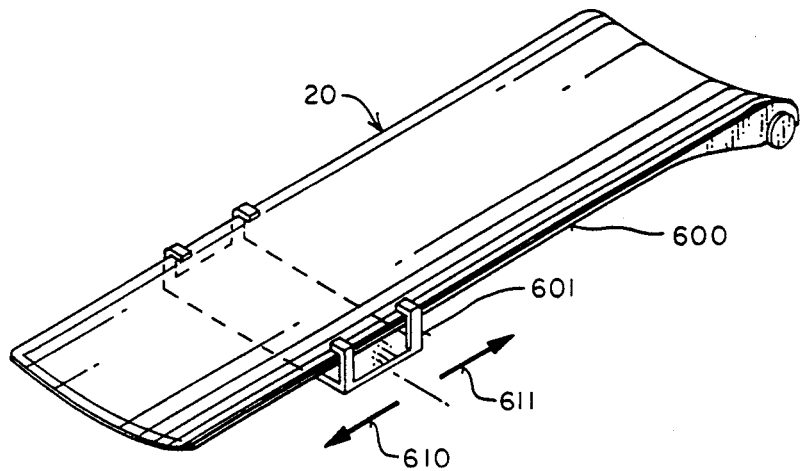
FIG_6A
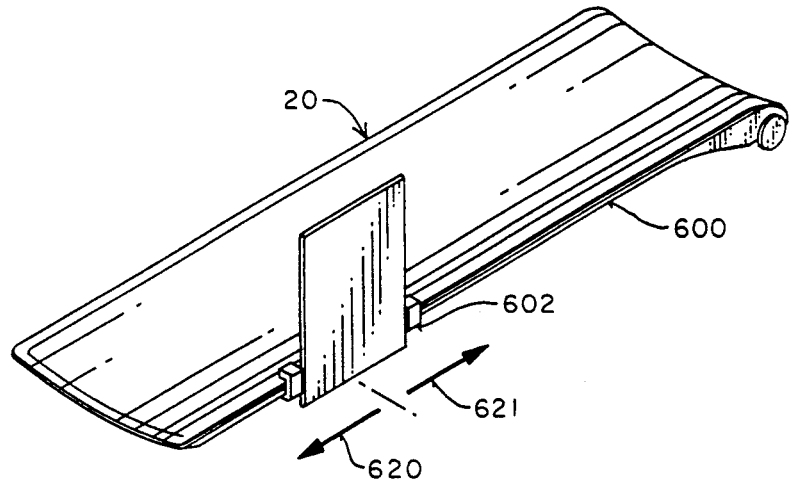
FIG_6B
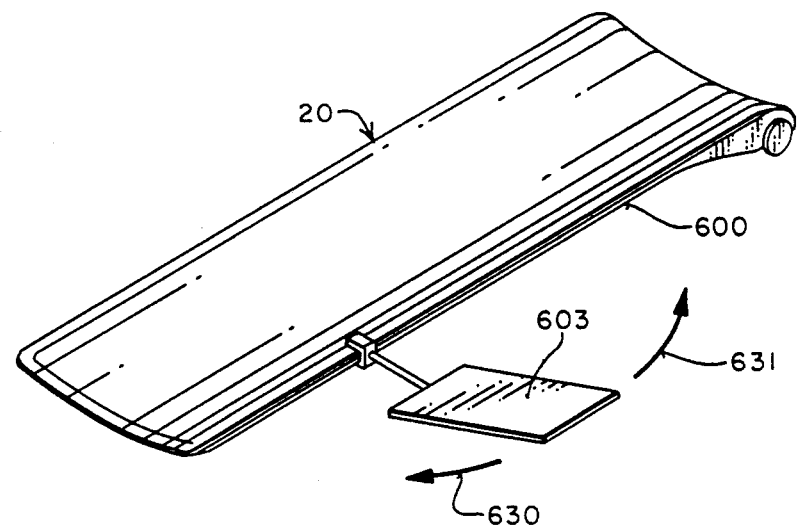
FIG_6C

FIG_6D
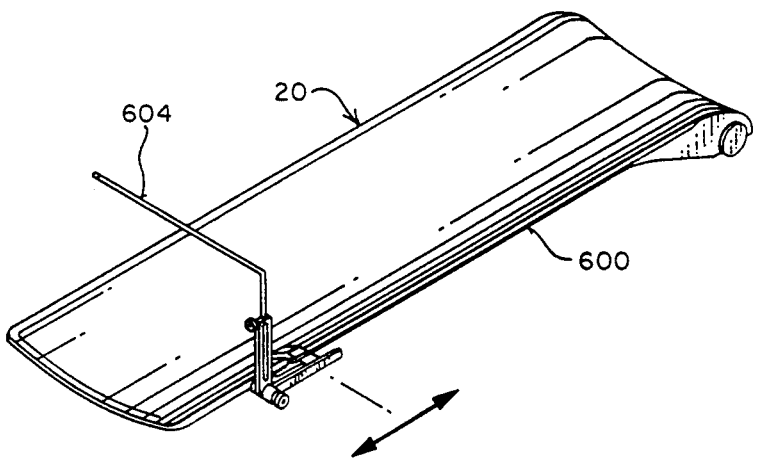
FIG_6E
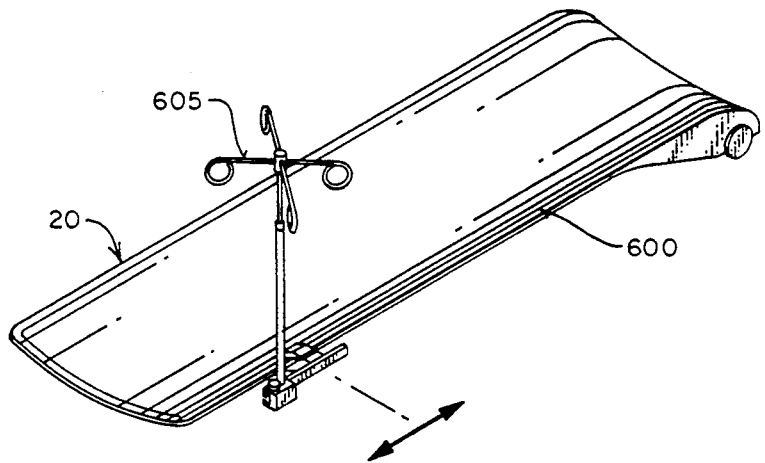
FIG_6F
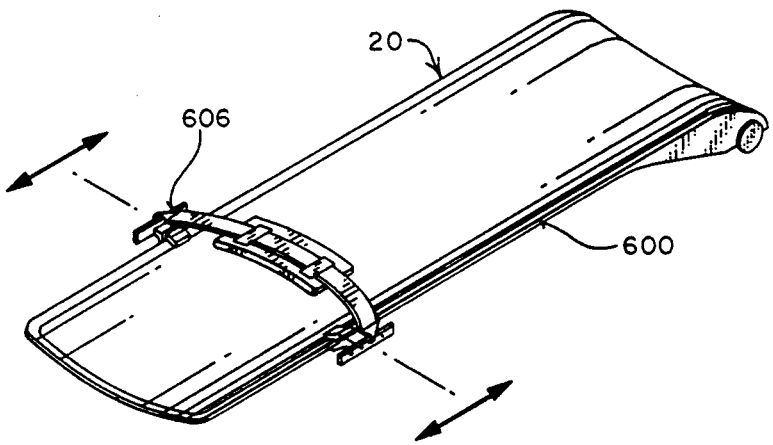

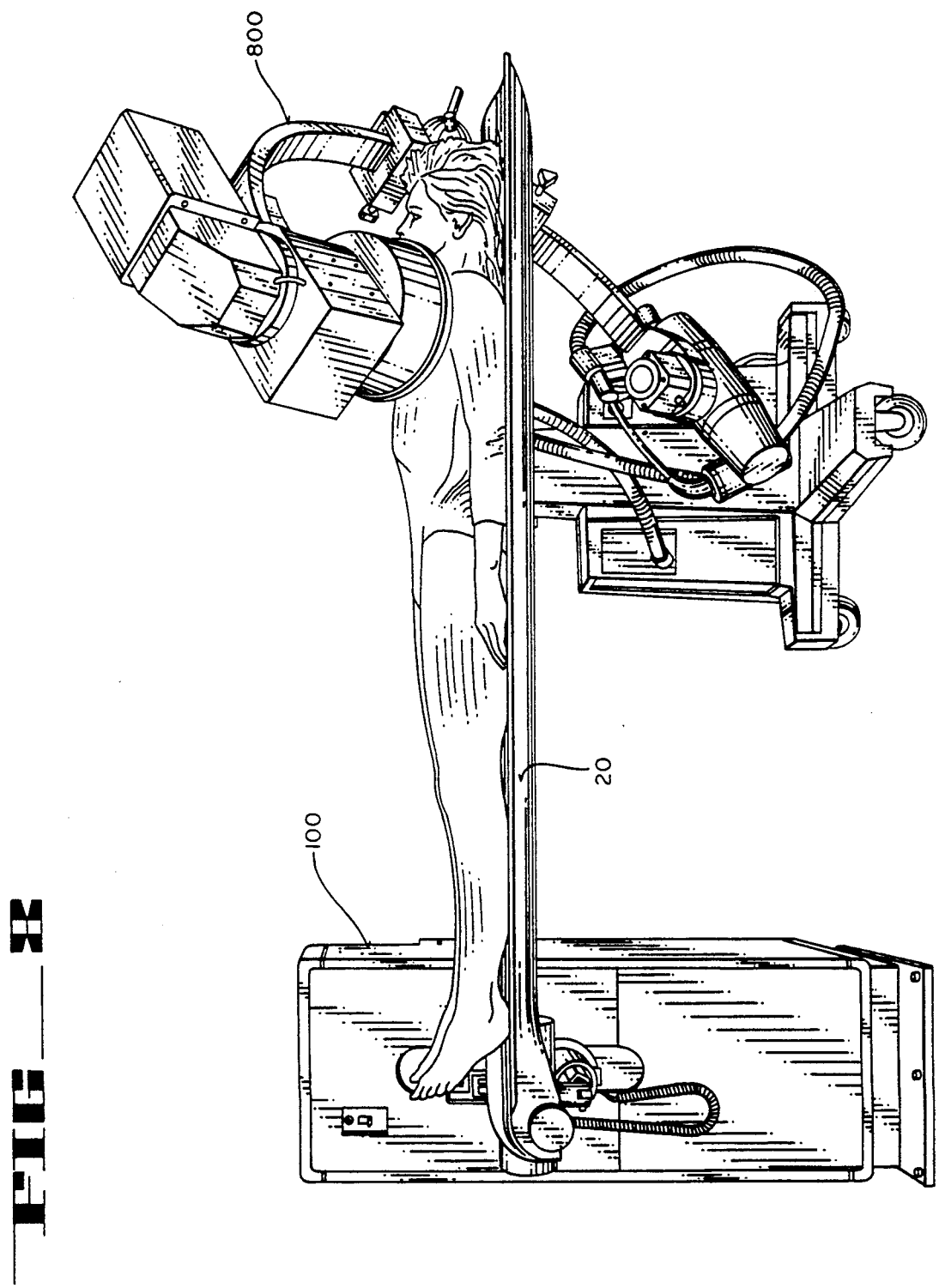
FIG—11

PATIENT SUPPORT TABLE

This is continuation of application Ser. No. 07/616,677, filed Nov. 21, 1990, now U.S. Pat. No. 5,131,105.

BACKGROUND OF THE PRESENT INVENTION

1. Field of the Present Invention

The present invention relates to an apparatus to support patients during medical procedures. More particularly, the present invention is directed to a movable patient support apparatus which has a removable surface that is interchangeable with a variety of configurations each of which are generally constructed of x-ray translucent material.

2. Prior Art

There exists a large variety of patient tables for medical applications, each of which is generally functional within a narrow range of clinical procedures due to its singular table top design as well as its overall configuration. However, in all cases, the table consists of two or three basic elements. Generally there is a table attached to a supporting mechanism and a means to move the table in various directions, including up and down. The moving mechanism may be manually operable or may be power assisted in many directions other than merely up and down. The ability to move the patient, once they are on the table is of importance to clinicians, as well desirable for accessibility to many of today's modern medical diagnostic or therapeutic devices, such as x-ray equipment.

The final configuration of a particular patient support unit is arrived at after contemplation of the various modes and methods available for support and mobility for the types of surgical access required, as well as satisfying the many conflicting clinical requirements.

Support structures for the patient table are generally divided into three types, namely base mounted, end mounted and side mounted. Additionally, a number of combinations or variations may also be constructed.

The base mount configuration is traditionally associated with a standard operating table. It is a support means whereby the table is attached to the support structure directly underneath the table. Examples of a base mounted configuration are described in U.S. Pat. No. 4,387,888, Marinakis; U.S. Pat. No. 4,540,165, Green et al.; U.S. Pat. No. 4,146,793, Bergstrom et al. and U.S. Pat. No. 3,814,414, Chapa.

Advantageously, the base mounted configuration permits unrestricted access at least one end, both sides and the top of the table (of course this is limited at the end having the base). Additionally, the base mount configuration takes up a minimum of floor space, a restricting limitation that must be considered when ascertaining the requirements for a patient support device. While the base mount configuration may be satisfactory for many medical procedures, such a configuration severely limits access from beneath the table as would be required with x-ray equipment imaging through the patients body in the area where the base mount resides.

Accessibility from beneath the table can be improved by having the table cantilevered from the base mount. Such tables are described in publications by SPECTRUM X-RAY CORPORATION and TECNOMED USA. Both tables provide for a floating table top with a reduced base mount section stand. Although accessibility is vastly improved over the traditional base mount configuration, the table becomes exceedingly long (over 9 feet), thus requiring a larger area for the table. Additionally, the cantilevered tables have exhibited tendencies of instability when fully extended.

The side mount configuration improves accessibility to the underside of the table, as well as above the table, both ends and the side opposite the attachment. An example of a side mounted configuration is described in U.S. Pat. No. 3,843,112, McDonald. The table is pivoted to one end of a horizontal arm, the other end of the arm being pivoted adjacent to the top of the pedestal so that the table can be supported outwardly from the pedestal in cantilevered fashion and moved to various adjusted positions. Disadvantageously, such a configuration requires relatively large floor space and restricts access on the side of the attachment and the base mount.

Another example of a side mounted configuration is described in U.S. Pat. No. 3,778,049, Viamonte, Jr. ('049). The patient support in the '049 patent provides for a cradle rather than a flat table, however, the concept of using a side support could be employed with a flat patient table. As in McDonald, the accessibility of the area underneath the table is vastly improved over the base mounted configuration. However, the ability of the clinician or support staff to access the patient on the sides is limited to the side opposite the support mount and both ends. While the side support provides the accessibility required by x-ray equipment and personnel, the design is not conducive to medical applications requiring patient access on either or both sides of the patient.

The third configuration generally used, depending on the clinical application is an end mount table. Although, the end mount configuration allows access to both sides, as well as the top and bottom of the table, one end of the table is inaccessible. For diagnostic or therapeutic purposes, this arrangement may be acceptable. However, for surgery, the anesthesiologist and anesthesia equipment are typically positioned at one end of the table. If the other end of the table were inaccessible due to the support mounting, the medical staff would be restricted in the their movements around the table. This may pose problems in an emergency situation.

Various designs for patient tables and the support structure have been discussed. In addition to the general configuration of the table and its support element, the ideal configuration permits the elevation and tilt of the patient in both the longitudinal plane (positive longitudinal tilt is known as Trendelenberg and negative longitudinal tilt is known as reverse Trendelenberg) and the lateral plane.

Additionally, tables may be designed to "float" the patient relative to the support mount. A floating table is one which moves in a predetermined plane on bearings mounted in a frame which is affixed to the support mount. While floating tables are ideally suited to radiology procedures, such configurations are not deemed acceptable for surgical procedures. Their unacceptability for surgical procedures is result of the patient's tethering to anesthesia equipment or other life support equipment.

For any given clinical procedure, there appears to be an optimum table design. Given specific requirements of accessibility and floor space allotments, no one particular design appears to be suited for all clinical applications. The configuration of the table, including the mounting means, chosen for a particular function is generally a collection of trade-offs made to enable the clinicians to perform their functions and have adequate equipment access, as well as using the minimal amount of floor space.

Other factors that must be considered when configuring a patient support unit is the material used to fabricate the table. To minimize x-ray transmission loss through the table, the table is fabricated from carbon fiber materials. Often, the table will not be flat but will be slightly dished, such that the patient may be made comfortable without the need for thick pads. Although the cost of carbon fiber material is high compared to an equivalent table made from stainless steel or other metals, the ability to image through the table is a controlling factor. However, attaching a carbon fiber table top to the support structure is a difficult task since all the load must be transferred and contact pressures become very high. Most commonly, carbon fiber tables are supported from underneath (i.e. base mounted) eliminating the issue of contact pressure. Tables mounted from the sides or ends, generally have a very high cantilever load and the means of mounting is no longer a trivial matter.

An additional factor to consider for providing for a table configuration is the alternatives of either having a fixed installation, where the table is fixedly mounted to the floor and is not readily moveable or having a mobile table, where the table is moveably moved from room to room as required. Often, clinical procedures will be performed in a room that does not make use of a particular table that is already in the room. One example, is the situation in which a general surgery table is moved out and replaced with an orthopedic fracture table. If the table is mobile, space efficiency is improved. However, the present mobile tables do not have the clinical utility or rigidity of fixedly mounted installations.

In summary, the prior art describes attempts to arrange the various design elements in a relatively effective manner that achieves clinical utility across a narrow range of medical procedures.

For example, a table configured to provide free access to the head and neck area is not optimally configured to perform whole body angiographic procedures. The wide range of clinical procedures requires a wide range of patient table configurations to accommodate them. The wide range of patient table configurations necessarily increases the total floor space allocation required within the hospital since multiple rooms with fixed installations of base units are required. While the mobile table configuration attacks this problem by allowing the table to be used in multiple locations, still, the mobile table, by virtue of its simplicity, cannot provide all the same motion, rigidity, and/or access with x-ray imaging equipment of a fixed installation. Finally, when multiple patients are being moved through a room with a fixed table, the table remains idle while the room is being cleaned and sterilized. This limits the efficient use of the available equipment.

Therefore, what is needed is a single table design that can be optimized for each of the various procedures without limiting the procedure or the use of any required imaging equipment. Ideally, the table design would incorporate the clinical utility and rigidity of a fixedly mounted installation with the space efficiency of a mobile design.

While an x-ray patient support apparatus as described in U.S. Pat. No. 4,912,754, Van Steenburg, ('754) has approached the ideal single table, the apparatus does not provide for interchangeable removeable table tops. The '754 patent describes an x-ray table top moveably supported by a shaft extending from a support mechanism and attached to the end of the table top. While the offset support connection to the table top provides accessibility to both sides, the top and bottom, and both ends, the table is not removeable from the support shaft and therefore cannot be interchanged with a table top of specific clinical design.

Ideally, an appropriate removeable table top mounted to a transport cart would enable multiple the table tops to be fitted onto the table base. Essentially, such a table design would combine the best aspects of both a fixedly mounted installation and a mobile device. Such a design would decrease room preparation time, increase space efficiency and clinical utility. Furthermore, for any fixedly mounted installation, the adaptability of the table that is applicable to a larger variety of clinical procedures would be beneficial to a medical facility, both in efficiency in the use of time, as well as the quality of patient care.

Additionally, the optimal table design would satisfy a sufficient number of clinical requirements at a low enough cost such that the table could be used as an adjunct to more complex fixedly mounted installations.

SUMMARY AND OBJECTS OF THE PRESENT INVENTION

One object of the present invention is to provide an x-ray translucent support apparatus, accessible at two sides, two ends, and the top and bottom.

Another object of the present invention is to provide a support apparatus adaptable to a variety of clinical applications by using removeable, interchangeable table tops, specifically designed for clinical procedures, such as for vascular procedures, urological procedures and for neurological procedures, etc.

These and other objects of the present invention are provided for by a patient support table comprising a first patient support surface. The first patient support surface, in a preferred embodiment, is comprised of an x-ray translucent material such as carbon fiber. The first patient support surface is substantially planar in shape and has a first end, a second end, a third end, a fourth end, and a top. The first end of the patient support surface is opposite to the second end, the third end is opposite to the fourth end, and the third and fourth ends are spaced farther apart than the first and second ends. In a preferred embodiment, the top of the first patient support surface is for supporting a patient and is slightly concave in shape at a central point. The patient support table also comprises a support, the support being affixed to the first end of the first patient support surface at a first end of the support and extending beyond the third end of the first patient support surface. The support is affixed in such a manner that the first patient support surface may be interchanged with a second patient support surface, wherein the second patient support surface has all of the properties of the first patient support surface. The patient support table finally comprises a base. The base is affixed to a second end of the support. The base allows positive and negative longitudinal tilt (Trendelenberg and reverse Trendelenberg), positive and negative lateral tilt, and height movement of the first patient support surface. The base provides a means for rigidly supporting the first patient support surface at a predetermined attitude and position.

BRIEF DESCRIPTION OF THE DRAWINGS

The present invention is illustrated by way of example and not limitation in the figures of the accompanying drawings in which like references indicate similar elements and in which:

FIG. 1 is a front view of the support mechanism, the table top and the main support shaft of the preferred embodiment.

FIG. 2 is a side view of the apparatus from the foot of the patient showing the support shaft and motorized mechanism.

FIG. 3a is a detailed view of the motorized assembly for controlling lateral tilt and Trendelenberg.

FIG. 3b is a detailed cutaway view of the motor assembly for controlling Trendelenberg and reverse Trendelenberg.

FIG. 3c is a detailed cutaway view of the mechanism used for support and lateral tilt in the preferred embodiment.

FIG. 4 is a detailed view of the hand-held control unit.

FIG. 5a, 5b and 5c are perspective views of the table top, and the support arm showing the attachment point in detail. FIG. 5a shows the table attached to the shaft. FIG. 5b shows a cross-sectional view of the support mount for the table after it has been attached. FIG. 5c shows how the table may be detached from or attached to the shaft.

FIGS. 6a-6f are perspective views of several accessories for use in alternative embodiments including:
  (a) a film cassette holder;
  (b) a lateral film cassette holder;
  (c) an arm board;
  (d) an anethesia screen holder;
  (e) a intravenous (IV) pole; and
  (f) a patient restraint strap.

FIG. 8 shows the apparatus with a C-arm x-ray unit into operating position for examination of a patient.

DETAILED DESCRIPTION

Figure 7A:
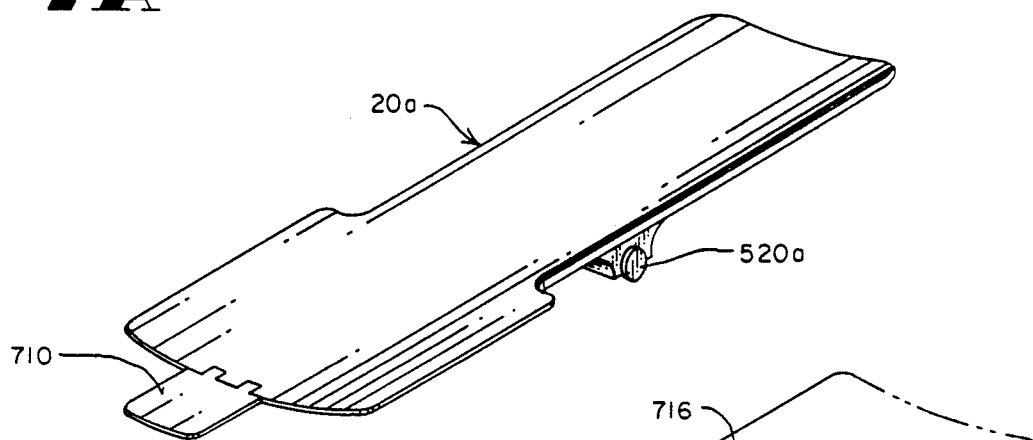
FIGS. 7a-7c are perspective views of alternative embodiment of the surgical table top including:
  (a) a carbon fiber neuro-angiographic table top;
  (b) a 2-way floating table top; and
  (c) a urological table top.

A patient support apparatus is described that is modular and is quickly configured for a variety of clinical procedures. The preferred embodiment also provides a table top that is x-ray translucent. In the following description, numerous specific details are set forth such as specific dimensions, materials, etc. in order to provide a thorough understanding of the present invention. It will be obvious, however, to one skilled in the art that the present invention may be practiced without these specific details. In other instances, well-known procedures and materials have not been described in detail in order to not unnecessarily obscure the present invention.

Referring to FIG. 1 patient support table 100 utilizes a support structure formed by a rectangular support tower 10. Support tower 10 provides a support shaft 150 to which table top 20 is attached. Table top 20 is easily removable from shaft 150. Table top 20 is removed by rotating the table approximately 20° in the direction indicated by arrow 50 since table 20 is coupled using a "hook" type attachment. This attachment mechanism is discussed in more detail with reference to FIGS. 5a through 5c below. The simplicity with which table top 20 may be attached to or detached from tower 10 increases the clinical utility of the system. A patient may be placed on table top 20 in an area other than the room where support tower 10 resides. This is important since tower 10 must be attached to the floor in which tower 10 resides. While resting on table top 20, the patient can be moved to support tower 10 via a transport cart or gurney. By using at least two such table tops, one procedure can be performed in the room where tower 10 is located while a second patient is prepared on a second table top. This is especially useful in multiple patient emergency situations.

In the preferred embodiment, tower 10 is attached to floor 130 of the room in which tower 10 resides using screws 131. Screws 131 are attached through apertures in base plate 132 of tower 10 providing a stable and rigid platform for table top 20. In an alternative embodiment base platform 132 may be counter weighted or attached in another method which allows apparatus 100 to remain stable.

Shaft 150 passes through a vertical slot 101 in the side of the support tower 10. Vertical slot 101 allows positive and negative elevation of table top 20 in the directions shown by arrows 60 and 61. Table 20 may be set to any desired height within the present table elevation limits of 29" to 46". The limits set forth in the preferred embodiment are merely illustration purposes only and in no way limit the scope of the present invention. Also, Trendelenberg and reverse Trendelenberg of typically 20°, but up to 90° indicated by arrows 70 and 71 is possible due to the mechanism within tower 10 which rotates shaft 150 in the clockwise and counterclockwise directions.

Referring to FIG. 2, a positive and negative lateral tilt of table 20 (roll) is also permitted using the motorized mechanism of the preferred embodiment. A positive or negative 20 degree rotation in directions represented by arrows 250 and 251 may be accomplished, as shown by the side view in FIG. 2. The elevation, Trendelenberg and lateral tilting of table top 20 is performed by the transmission gear reduction assemblies and motors shown in the cutaway view of tower 10 in FIG. 2.

Each motorized mechanism shown in FIG. 2 in tower 10 of the preferred embodiment is driven from a pulse width modulation (PWM) driver. In an alternative embodiment, other motor drive methods may be used such as hydraulics. In the preferred embodiment, DC servo motors are used for good power efficiency and control capability. The driver consists of PWM switched circuits controlled by acceleration and deceleration ramps in order to provide smooth start up and stopping characteristics.

A first motor 210 is shown at the bottom of tower 10 and is used to control elevation of table top 20. This is performed by motor 210 which drives a belt 211. Belt 211 is further coupled to a gear reduction assembly 212. Gear reduction assembly 212 is coupled to shaft 213 which is then coupled to differential 214. Gear reduction assembly 212 converts the rapid rotary motion of motor 210 to rotary motion with lower RPM and higher torque to rotate drive shaft 213. Shaft 213, in turn, drives differential assembly 214 which converts the rotary motion about a horizontal axis to a rotary motion about the vertical axis. The rotary motion in the vertical axis from differential 214 drives threaded shaft 215. The rotary motion of threaded shaft 215 causes block 216 to move up and down within tower 10. This vertical movement of block 216 causes assembly 200 to move up and down. Assembly 200 comprises the remainder of the motors and mechanisms for Trendelenberg and lateral tilting of table 20. Since assembly 200 is coupled to shaft 150, elevation of assembly 200 causes elevation of shaft 150.

Assembly 200 comprises two additional motors 220 and 260 as shown in FIG. 2. Motor 260 controls Trendelenberg and reverse Trendelenberg of table 20 in the directions 70 and 71 shown in FIG. 1. Motor 220, is used for driving a mechanism (discussed in more detail below) which causes table 20 to tilt in lateral directions 250 and 251 shown in FIG. 2. Motors 220 and 260 along with the corresponding mechanism and assembly is affixed to plate 250 which in turn slides up and down along track poles 251, 252, and 253. Track poles 251, 252 and 253 allow rigid support for assembly 200. This also provides rigid support for shaft 150 which holds table 20 at a predetermined attitude and position. A more detailed representation of assembly 200 is shown and discussed with reference to FIGS. 3a–3c.

As shown in FIG. 3b, motor 260 is affixed to plate 250. Motor 260 drives worm gear 365 to convert rotary motion of motor 260 about a horizontal axis to rotary motion about an approximately vertical axis. This rotary motion about an approximate vertical axis of shaft 366, in turn, drives a worm gear assembly 367 shown in the cutaway view in FIG. 3b which drives gear 368 residing in assembly 340. The driving of gear 368 causes the rotary motion of shaft assembly 150 for Trendelenberg tilting of table 20. The rotation, therefore, of shaft 150 via gear 368, gear assembly 367, and 365 by motor 260 causes the rotation of shaft 150. This, in turn causes Trendelenberg and reverse Trendelenberg of table 20 in directions 70 and 71 shown in FIG. 1.

As is shown in FIG. 3a, motor 220 is also affixed to plate 250 using mounting brackets 331 and 332. The drive shaft of motor 220 is coupled to a primary sprocket 350 which is used for driving chain 352. Chain 352 in turn drives secondary sprocket 353 which in turn drives a secondary shaft 370 located within shaft 150 for causing lateral tilt of table 20. A more detailed discussion of this mechanism is discussed below with reference to FIG. 3c.

Motor 220 provides rotary motion to a drive shaft 370 having a threaded bore which resides in the center of shaft 150 as shown in FIG. 3c. The rotary motion, caused by motor 220 on drive shaft 370, converts the rotary motion of motor 220 into a linear motion of a threaded shaft 230. As illustrated in FIG. 3c, support shaft 150 is equipped with a flange assembly 310 rotatably mounted at point 360. In order to implement lateral tilt of table 20 in directions 250 and 251 shown in FIG. 2, threaded shaft 230 is attached to flange 340. Flange 340 is coupled to the flange assembly 310 at one end, and to screw shaft 230 via coupling shaft 346. Coupling shaft is attached to screw shaft 230 at pivot 347 and to flange 340 at pivot 345. Pivot 345 allows the linear motion in directions 350 and 351 of threaded shaft 230 into a rotary motion of the auxiliary shaft 345 about the pivot 360 in directions 250 and 251. This causes lateral tilt of table top 20. In other words, movement of threaded shaft 230 in direction 350 is translated into rotational movement of flange assembly 310, causing movement of auxiliary shaft 345 in direction 250, a positive lateral tilt ("tilt in" towards tower 10). Conversely, movement of screw shaft 230 in direction 351 causes movement of auxiliary shaft 50 in direction 251 (as shown on both FIGS. 2 and 3c), a negative lateral tilt ("tilt out" away from tower 10).

Movement of thread shaft 230 in directions 350 and 351 is accomplished by rotation of drive shaft 370. Drive shaft 370 is driven by motor 220 in tower 10. As discussed previously, this is accomplished, as shown in FIG. 3a, via primary sprocket 351 coupled to motor 220, which drives chain 352 which then drives secondary sprocket 353 coupled to drive shaft 370. Drive shaft 370 resides in support shaft 330 and is mated to threaded shaft 230 via a threaded bore 371 in the center of drive shaft 370. Therefore, when drive shaft 370 is rotated by motor 220, threaded bore 371 is also rotated thus causing screw shaft 230 to move in either direction 350 or 351.

Table elevation, Trendelenberg and lateral tilt is controlled using hand-held control unit 170 which is coupled to circuitry driving motors 210, 220 and 260 in tower 10 via line 171 as shown in FIG. 1. A detailed representation of hand-held control unit 170 is shown in FIG. 4. Positive elevation of table top 20 in direction 60 shown in FIG. 1 is controlled by depressing button 401 and negative elevation is accomplished by depressing button 402. Trendelenberg tilting 70 as shown in FIG. 1 is accomplished by depressing button 403. Of course, if table 20 were mounted in the opposite direction from that shown in FIG. 1, this direction would be reverse Trendelenberg. Reverse Trendelenberg 71 for the orientation shown in FIG. 1 is achieved by depressing button 404. Lastly, positive lateral tilt 250 ("tilt in") shown in FIG. 2 is accomplished by depressing button 405, and negative lateral tilt 251 ("tilt out") is achieved by depressing button 406. Each of the buttons must be held throughout the entire motion. Once a button is released, table motion will stop. Table motion will also stop at the table motion limits (elevation −29" to 46", Trendelenberg ±20°, and lateral tilt ±20°), and an auditory tone will sound accompanied by the illumination of light 180 on tower 10 shown in FIG. 1. Finally, control unit 170 comprises an "Auto Level" button 410 which will automatically level the table at its current elevation. This function is useful for floating tabletops in alternative embodiments such as 20b shown in FIG. 7b when used with tower 10. This function allows the floating table to be levelled automatically so that it can unlocked from its frame and moved to a new position. This is useful because such an operation should not be performed when the table is oriented at an angle.

As illustrated in FIGS. 5a and 5b, table top 20 incorporates an attachment tab 510 in attachment sleeve 520 that mates with the T-shape of table support shaft 345 at points 511. With no patient on table 20, table 20 may be attached to shaft 345 by placing it at an approximate 20° angle relative to support shaft 345 and moved in direction 501 as shown in FIG. 5c. Table 20 may then be rotated in direction 500 into the position as shown in FIG. 5a after tab 510 engages with one point 511 on support shaft 345. Alternatively, with a patient resting on table 20, attachment of table top 20 to table support shaft 345 may be implemented by simply rotating the support shaft 345 to approximately 20° using control unit 170 and laying the table attachment sleeve 520 of table 20 over table support shaft 345 with the attachment tab 510 under one groove 511. Then, support shaft 345 may be rotated back 20° using control unit 170 to engage the attachment tab 510 with groove 511. Once groove 511 engages with tabs 510, shaft 345 may be used to lift table top 20 off of a transport cart or gurney, for example. After mating with support shaft 345 as shown in FIG. 5a, gravity and patient load securely hold table top 20 to shaft 345 due to the high contact forces present. Because attachment tabs 511 are symmetric on table support shaft 345, table top 20 can be mounted to table support shaft 345 from either direction. This allows table top 20 to be used in multiple rooms where orientation of the table top relative to the support tower 10 is determined by the room size or other considerations. Note that disk 160 is affixed to the end of table support shaft 345 to prevent table 20 from sliding off of shaft 345. In one alternative embodiment, a square table support shaft instead of 345 may be used with a square sleeve embedded in table top 20. In other alternative embodiments, other symmetrically shaped shafts of the table support shaft and attachment sleeve 520 may be used to hold table 20 securely.

As shown in FIG. 5a and 5b, table top 20 of the preferred embodiment is comprised of a foam core 530 overwrapped with carbon fiber reinforced unidirectional tape 540. Each layer of carbon fiber tape 540 is wrapped around core 540 and sleeve 520 in different directions for each layer to increase structural strength as shown in FIG. 5a and 5b. The tapered design concentrates strength at attachment sleeve 520. Attachment sleeve 520 is comprised of high-strength steel and is bonded into table top 20 during the manufacturing process, thereby increasing the strength of the bond by spreading load forces over the area of sleeve 520. Note that design of the preferred embodiment incorporates no metal other than in sleeve 520 forming a near perfect x-ray translucent support surface for angiographic studies of the complete body. Several layers of graphite tape and glass cloth 540 cloak metal sleeve 520 to form the attachment point of table top 20.

In alternative embodiments, table top 20 may be comprised of other x-ray translucent materials with sufficient structural strength. Table top 20 may be comprised of an x-ray opaque material for a table that is not used in x-ray procedures in other alternative embodiments. In the case of standard, routine angiographic procedures, access to the entire body is required for both clinicians and the x-ray imaging equipment, as is allowed by the preferred embodiment.

As illustrated in FIGS. 6a-6f, table top 20 is fabricated with a lip 600 on its bottom edge to permit standard clinical procedure accessories such as film cassette holder 601, arm board 603, IV pole 605, etc. to be attached to table top 20. Although FIGS. 6a-6f show accessories 601-606 used on table 20, they could also be used on alternative embodiments of table top 20 provided an attachment lip 600 is present, and other accessories than those shown in FIGS. 6a-6f may be used with table 20.

A film cassette holder 601 may be fabricated to slide along the length of table top 20 as illustrated by arrows 610 and 611. A lateral film cassette holder 602, as shown in FIG. 6b may also be attached to the side of table top 20. Motion may be made along the length of the table top 20 and is uninhibited by any support structure. Cassette 602 can be moved in directions 620 and 621 along the table. Using the same techniques as lateral cassette holder 602, an arm board 603 shown in FIG. 6c may be installed on either side of the table top 20 and rotated, if required, in directions 630 and 631 for proper positioning. Additionally, an anesthesia screen holder 604 shown in FIG. 6d and an intravenous (IV) pole 605 shown in FIG. 6e may be attached to the side of table top 20 using lip 600. Lastly, patient support strap 606 affixes to lip 600 as shown in FIG. 6f. Support strap 606 may be used to secure a patient to table 20 for certain procedures and/or table movements.

Alternative embodiments of table top 20 are illustrated in FIGS. 7 (a)-(c), however, it should be clear that other table configurations are also possible within the spirit and scope of the present invention. The alternative table configurations are dictated by the requirements of particular clinical procedure to be performed.

In reference to FIG. 7a, one alternative configuration of a carbon fiber table top 20a is illustrated. This configuration is a carbon fiber table intended for neuro-angiography procedures. Structural fabrication specifications are generally the same as the standard table described in FIGS. 5a and 5b. However, access to only the upper half of the body is required. Therefore, the attachment point 520a is located approximately at the mid-point of the table, slightly below the femoral artery. This mid-table attachment point increases rigidity. Total access to the patient is still possible due to the large offset from tower support 10. Table top 20a is fabricated to follow the contours of the upper torso and head. The head section 710 is removable. This permits the use of a carbon fiber, x-ray translucent Mayfield head holder (not shown).

Figure 7B:
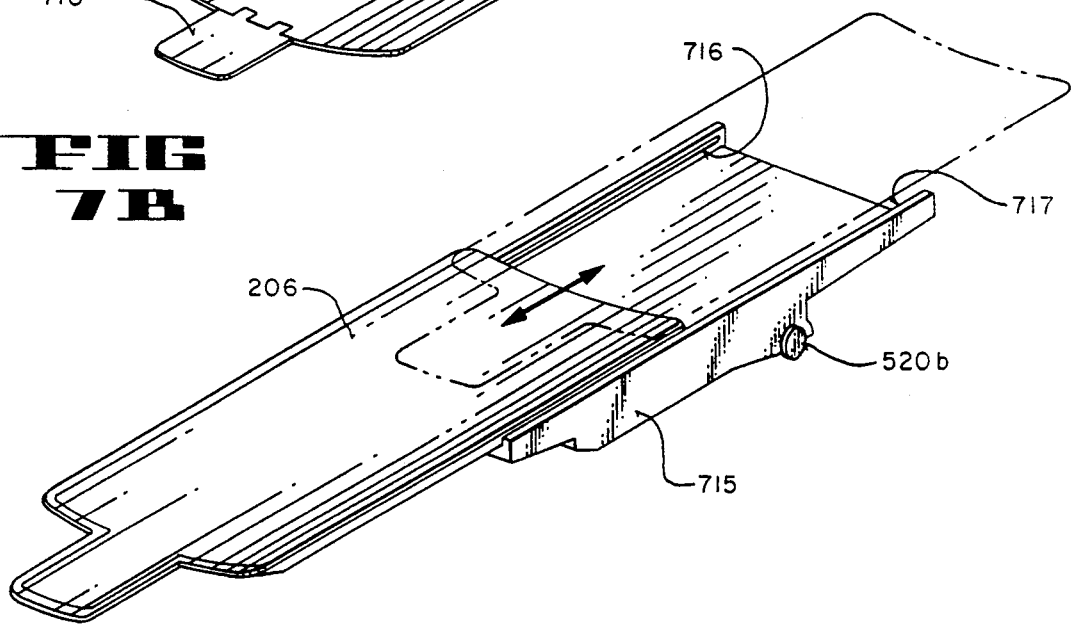

The second table configuration 20b shown in FIG. 7(b) is quite different from the first alternative embodiment, in that is describes a floating top. Floating table top 20b rests on a secondary support top 715 which has tracks 716 and 717 upon which the table top 20b can slide as shown in FIG. 7b. This is useful for other types of x-ray studies such as myelography.

Figure 7C:
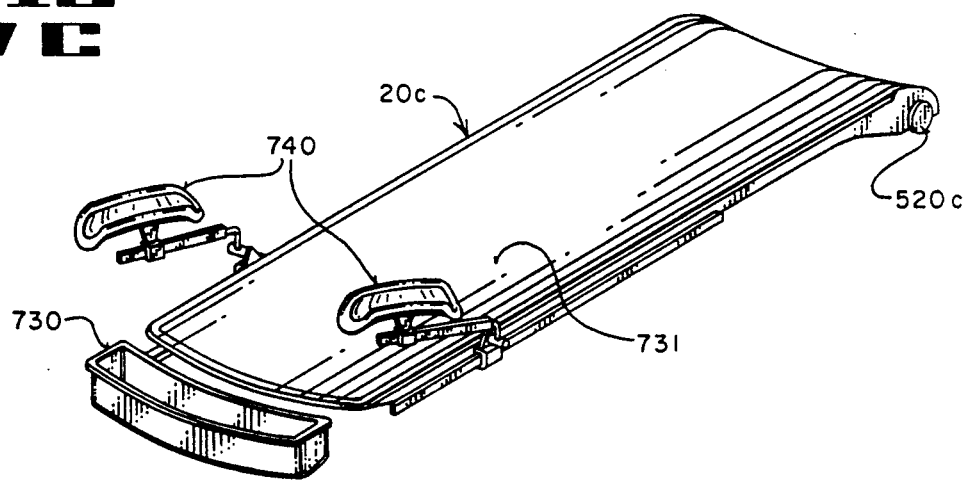

A third table configuration, as shown in FIG. 7c illustrates a urological table top 20c. The table top 20c is comprised of several sections. The upper section 731 has a more concave top surface, thus permitting drainage into drain pan 75. As the patient's legs are elevated during a urological procedure, leg stirrups 740 are provided to rest the patient's legs upon. Furthermore, due to the nature of clinical urological procedures, the table top 20c is shorter to enable the clinician better access to the patient. Although, three alternative table top configurations have been described, many other table designs can be developed using the modular concept of this invention.

The preferred embodiment 100 of the present invention is shown in FIG. 8 with a C-arm x-ray unit 800 in place for performing a complete angiographic study of the body. As is shown in FIG. 8 with a patient resting on table top 20 of apparatus 100, the C-arm x-ray unit 800 has access to the entire body of the patient. Since the C-arm x-ray unit 800 may be moved about the table in any orientation to allow a complete angiographic study of the body as well as access to the patient for clinical/surgical procedures along with the attending equipment and personnel, the advantages of supporting a table top such as 20 in the manner shown in the preferred embodiment can be appreciated.

Thus, what is described is an apparatus that permits longitudinal tilting (Trendelenberg and reverse Trendelenberg) and lateral tilting, as well as vertical elevation. Further, the means for provided removeable table tops without the use of tools has been described.

What is claimed is:

1. Apparatus for supporting a patient, comprising:
   a base having an upright extension;

a patient table means having a longitudinal and a transverse axis;

a table elevator means moveably secured to said extension for up and down movement of said extension with respect to said base;

a first longitudinally elongated table support member having a first axis extending generally parallel to one of the axes of said table and having a proximal end supported upon said elevator and a distal end adjacent said table;

a second longitudinally elongated table support member having a proximal end adjacent said elevator, and a distal end adjacent said table and extending at an angle to said first member;

said table being moveably secured to said first member at the distal end thereof so as to permit said table to pivot about a second axis generally parallel to another of said table axes, said second axis being adjacent to and beyond a perimeter of said table;

said second member being axially extendible to urge said table means about said second axis;

whereby said table may be canted about one axis parallel to one of said table axes as well as tilted about another axis parallel to the other of said table axes.

2. Apparatus as in claim 1, in which the non-distal portions of said first and second support members are coaxial.

3. Apparatus as in claim 1, in which said members of said table spacing and support means are located substantially within a single upright vertical plane.

4. Apparatus as in claim 1, in which the axes of said longitudinally elongated members define a plane generally parallel to the axis of said upright extension of said base.

5. Apparatus as in claim 1, in which said second member passes axially centrally through said first support member.

6. Apparatus as in claim 1, in which said first support member is rotatably mounted upon said elevator means for movement about the axis of said first member.

7. Apparatus as in claim 1, in which said proximal ends of said first and second elongated support members define a common junction with said elevator means.

8. Apparatus as in claim 1, in which said table means joins said first member adjacent one corner of said table means.

9. Apparatus as in claim 1, in which said elongated support members and the transverse axis of said table are oriented substantially parallel to each other.

10. Apparatus as in claim 1, in which the distal end of said second longitudinally elongated member is located below that of said first elongated member.

11. Apparatus as in claim 1, which further includes a first drive means for providing a linear motion to cause said second elongated member to extend axially.

12. Apparatus as in claim 1, which further includes a link member pivotally connected between said table means and the distal end of said second member.

13. Apparatus as in claim 1, in which said table means includes a patient support table and an elongated supporting arm extending under and adjacent one edge of said table generally parallel to an axis of said table.

14. Apparatus as in claim 13, in which said supporting arm includes a portion extending between and pivotally joined to said distal ends of said first and second elongated support members, so as to enable the pivoting of said table about said second axis in response to the axial extension of said second member.

15. Apparatus for supporting a patient, comprising:

a base having an upright extension;

patient table means;

a table elevator means moveably secured to said extension for up and down movement with respect to said base, said elevator means including a first generally horizontally extending member, said member being elongated outwardly a first distance beyond said upright extension;

a first shaft rotatably supported upon said first member for movement about the shaft axis and extending outwardly from said upright extension at least said first distance;

said table being pivotally secured to said shaft at the end of said shaft opposite said elevator so as to permit angular movement of said table about a second axis which is adjacent to and beyond a perimeter of said table and is generally perpendicular to that of said shaft, said table being thereby rotatably supported by said first elongated member and said shaft for angular movement about perpendicular axes;

said first distance being sufficiently great to enable access to the supported end of said table means unimpeded by the proximity of said base and upward extension;

means extending to said table and supported on said shaft for transmitting a force to said table to move same about said second axis; and means for rotating said shaft about said shaft axis;

whereby said table may be canted about one axis as well as tilted about another axis perpendicular thereto.

16. Apparatus as in claim 15 in which said first member envelops said shaft.

17. Apparatus as in claim 15 in which said first member and said shaft are coaxial.

18. Apparatus as in claim 15 which further includes means extending to said table means and supported with the aid of said shaft for urging said table means about said second axis.

19. Apparatus as in claim 15 which further includes means extending to said table means and passing through and axially within said shaft for urging said table means about said second axis.

20. Apparatus as in claim 15 in which said means for urging said table means further includes a second elongated shaft within said first shaft and which is axially extendible from said first shaft to urge said table means about said second axis.

21. Apparatus as in claim 20 which further includes a link member pivotally attaching the end of said second shaft adjacent said table means to said table means.

22. Apparatus as in claim 15 in which one of the shaft ends adjacent said table means is offset relative to the other end.

23. Apparatus as in claim 15 which further includes means associated with said elevator means for rotating said shaft.

24. Apparatus as in claim 15 in which said table means is provided with a member adjacent one end thereof by which said table means is pivotally secured to said shaft.

25. Apparatus as in claim 15 in which said table means is comprised of a patient support table having a longitudinal axis and a transverse axis, and a elongated support member extending under and adjacent one edge of said table generally parallel to an axis of said table.

26. Apparatus as in claim 15 in which said elongated support member extends generally parallel to the transverse axis of said table.

27. Apparatus as in claim 26 in which said table and said support member are provided with complementary interlocking portions such that said table is easily removable by lifting same off of said elongated support member, and yet the weight of said table holds the same in secure engagement with said elongated support member.

28. Apparatus as in claim 15 in which said elevator is moved simultaneously with the rotation of said shaft, to cause said table means to be effectively tilted about an axis different from but parallel to that of said shaft.

29. Apparatus for supporting a patient, comprising:
a base having an upright extension;
patient table means;
a table elevator means moveably secured to said extension for up and down movement with respect to said base;
a shaft rotatably mounted for movement about the shaft axis upon said elevator, said shaft extending generally laterally of said upright extension and being elongated outwardly a first distance beyond said extension;
means for pivotally securing said table means to said shaft at the end of said shaft opposite said elevator so as to permit angular movement of said table means about a second axis generally perpendicular to said shaft axis and adjacent to and beyond a perimeter of said table, said table thereby being moveable about perpendicular axes;
said first distance being sufficiently great to enable access to the supported area of said table means unimpeded by the proximity of said base and upward extension.

30. Apparatus as in claim 29 which further includes means extending to said table means and supported with the aid of said shaft for urging said table means about said second axis.

31. Apparatus as in claim 29 which further includes means extending to said table means and extending through said shaft for urging said table means about said second axis.

32. Apparatus as in claim 31 in which said means for urging said table means further includes a second elongated shaft within said first shaft and which is axially extendible from said first shaft to urge said table means about said second axis.

33. Apparatus as in claim 32 which further includes a link member pivotally attaching the end of said second shaft adjacent said table means to said table means.

34. Apparatus as in claim 32 in which one of the shaft ends adjacent said table means is offset relative to the other end.

35. Apparatus as in claim 29 which further includes means associated with said elevator means for rotating said shaft.

36. Apparatus as in claim 29 in which said table means is comprised of a patient support table having a longitudinal axis and a transverse axis, and a elongated support member extending under and adjacent one edge of said table generally parallel to an axis of said table.

37. Apparatus as in claim 36 in which said elongated support member of said table means is pivotally secured to said shaft by said means for pivotally securing said table means.

38. Apparatus as in claim 37 in which said elongated support member extends generally parallel to the transverse axis of said table.

39. Apparatus as in claim 37 in which said table and said support member are provided with complementary interlocking portions such that said table is easily removable by lifting same off of said elongated support member, and yet the weight of said table holds the same in secure engagement with said elongated support member.

40. Apparatus as in claim 29 in which said elevator is moved simultaneously with the rotation of said shaft, to cause said table means to be effectively tilted about an axis different from but parallel to that of said shaft.

41. Apparatus as in claim 29 in which said shaft is rotatably mounted so as to constrain said shaft to a substantially horizontal position.

42. Apparatus as in claim 41 which further includes means secured to said elevator means for rotatably mounting said shaft for movement about the shaft axis and in a substantially horizontal position.

43. Apparatus as in claim 42 in which said means for rotatably mounting said shaft is substantially the sole support of said shaft.

44. Apparatus as in claim 29 in which said shaft is rotatably mounted and supported only at one end thereof upon said elevator means.

45. Apparatus as in claim 44 in which said shaft is rotatably mounted at said one end so as to constrain said shaft to a substantially horizontal position.

46. An apparatus for supporting a patient comprising:
a. a base fixedly attached to a floor;
b. a table for supporting a patient, said table having a transverse axis and a longitudinal axis, sides which are substantially parallel with said longitudinal axis; and ends which are substantially parallel with said transverse axis;
c. a support member coupled to said base and extending outward from said base and coupled at one of said ends of said table, said support member including:
 i. a means for rotation of said table about said transverse axis of said table, said means for rotation about said transverse axis comprising a first rotation axis at said one of said ends which is coaxial with said support member;
 ii. a means for rotation of said table about said longitudinal axis of said table, said means for rotation about said longitudinal axis having a second rotation axis which is adjacent to one of said sides of said table, is beyond a perimeter of said table, and is extended outward from said base in said support member; and
d. a means for elevating said support and said table with respect to said base.

47. The apparatus of claim 46 wherein said means for rotation about said longitudinal axis comprises a first shaft which is coupled to a flange at one end of said support, said flange coupled to a rotatable pivot member which rotates at said second rotation axis, said flange for translating inward and outward movement of said first shaft to rotary motion of said table about said second rotation axis.

48. The apparatus of claim 47 further comprising a second shaft coupled to said rotatable pivot member which is further coupled to said table.

49. The apparatus of claim 48 wherein said means for rotation comprises a motor in said base coupled to said shaft.

50. The apparatus of claim 47 wherein said first shaft comprises a threaded shaft, and said threaded shaft is mated with a threaded drive shaft for causing said inward and outward movement of said threaded shaft.

51. The apparatus of claim 47 wherein said support member comprises a cavity coaxial with said support member and said first shaft is situated in said cavity.

52. The apparatus of claim 46 wherein the means for rotation about said longitudinal axis, said transverse axis, and said elevation means comprise pulse width modulation (PWM) drive motors.

53. The apparatus of claim 46 wherein said tilting about said transverse axis comprises Trendelenburg tilting.

54. The apparatus of claim 46 wherein said tilting about said longitudinal axis comprises lateral tilting.

55. The apparatus of claim 46 wherein the table is comprised of an X-ray translucent material.

56. An apparatus for supporting a patient comprising:
 a. a base fixedly attached to a floor;
 b. a table for supporting a patient, said table having a transverse axis and a longitudinal axis, sides which are substantially parallel with said longitudinal axis, and ends which are substantially parallel with said transverse axis;
 c. a support member coupled to said base and extending outward from said base and coupled at one of said ends of said table, said support member including:
  i. a means for rotation of said table about said transverse axis of said table, said means for rotation about said transverse axis comprising a first rotation axis at said one of said ends which is coaxial with said support member;
  ii. a means for rotation of said table about said longitudinal axis of said table, said means for rotation about said longitudinal axis having a second rotation axis which is adjacent to one of said sides of said table, is beyond a perimeter of said table, and is extended outward from said base in said support member, said means for rotation about said longitudinal axis comprising a first shaft which is coupled to a flange at one end of said support, said flange coupled to a rotatable pivot member which pivots at said second rotation axis, said flange for translating inward and outward movement of said first shaft to rotary motion of said table about said second rotation axis; and
 d. a means for elevating said support and said table with respect to said base.

57. The apparatus of claim 56 further comprising a second shaft coupled to said rotatable pivot member which is further coupled to said table.

58. The apparatus of claim 57 wherein said means for rotation comprises a motor in said base coupled to said shaft.

59. The apparatus of claim 56 wherein said first shaft comprises a threaded shaft, and said threaded shaft is mated with a threaded drive shaft for causing said inward and outward movement of said threaded shaft.

60. The apparatus of claim 56 wherein said support member comprises a cavity coaxial with said support member and said first shaft is situated in said cavity.

61. The apparatus of claim 56 wherein the means for rotation about said longitudinal axis, said transverse axis, and said elevation means comprise pulse width modulation (PWM) drive motors.

62. The apparatus of claim 56 wherein said tilting about said transverse axis comprises Trendelenburg tilting.

63. The apparatus of claim 56 wherein said tilting about said longitudinal axis comprises lateral tilting.

64. The apparatus of claim 56 wherein the table is comprised of an X-ray translucent material.

* * * * *